United States Patent [19]

Witty et al.

[11] Patent Number: 4,675,299
[45] Date of Patent: Jun. 23, 1987

[54] SELF-CONTAINED REAGENT PACKAGE DEVICE AND AN ASSAY USING SAME

[75] Inventors: Thomas R. Witty, Salt Lake City, Utah; Robert E. Curry, Ramsey, N.J.; Roger E. Smith, Bountiful, Utah

[73] Assignee: Becton, Dickinson and Company, Franklin Lakes, N.J.

[21] Appl. No.: 681,034

[22] Filed: Dec. 12, 1984

[51] Int. Cl.$^4$ ............................................. G01N 21/03
[52] U.S. Cl. ................................. 436/165; 436/808; 435/810; 422/58; 422/61; 422/102; 206/569; 356/246
[58] Field of Search ................. 422/57, 58, 61, 101, 422/102, 104; 206/569; 435/300, 301, 311, 810; 436/165, 807, 808; 356/246

[56] References Cited

U.S. PATENT DOCUMENTS

| | | | |
|---|---|---|---|
| 3,582,285 | 6/1971 | Hamilton | 422/61 |
| 3,825,410 | 7/1974 | Bagshawe | 424/12 |
| 3,932,141 | 1/1976 | Beall et al. | 141/325 |
| 4,090,850 | 5/1978 | Chen et al. | 422/101 |
| 4,160,803 | 7/1979 | Potts | 422/101 |
| 4,251,159 | 2/1981 | White | 422/58 |
| 4,272,478 | 6/1981 | Vihko | 422/58 |
| 4,383,041 | 5/1983 | Kutsusawa et al. | 435/291 |
| 4,387,164 | 6/1983 | Hevey et al. | 422/56 |
| 4,425,438 | 1/1984 | Bawman et al. | 422/57 |
| 4,534,939 | 8/1985 | Smith et al. | 422/61 |

FOREIGN PATENT DOCUMENTS 54440 4/1980 Japan ..................................... 422/61
WO82/03690 10/1982 PCT Int'l Appl. ................. 422/101

*Primary Examiner*—David L. Lacey
*Attorney, Agent, or Firm*—Richard J. Rodrick

[57] ABSTRACT

A self-contained reagent package device for an assay comprises a support member and a plurality of wells in the support member. All of the wells are capable of retaining liquids therein. At least one of the wells has an aperture at its bottom end for the passage of liquids therethrough. The one well includes a carrier to which a reagent is bound and further includes a porous filter positioned between the carrier and the aperture which is capable of retaining liquids used in the assay under normal atmospheric pressure conditions. The filter permits the passage of those liquids, including unbound and soluble substances, at increased pressure within the one well. Further, the filter is capable of retaining the carrier and substances bound thereto. At least one of the wells includes a predetermined amount of reagent therein. Another of the wells is empty so that the specimen to be assayed may be deposited therein. A removable protective cover is sealed over the open ends of the wells to maintain the incorporated reagents in stable form prior to use. A method for the performance of an assay using the above-described device is another aspect of the present invention.

21 Claims, 4 Drawing Figures

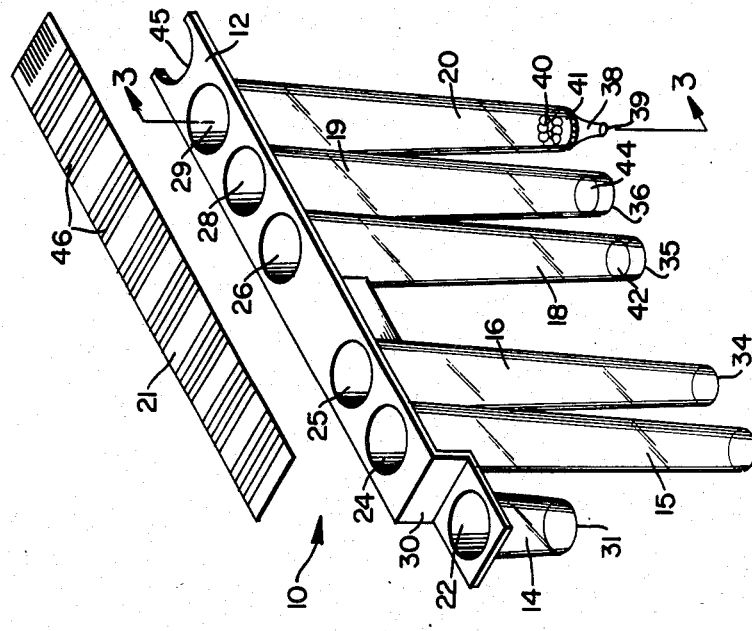
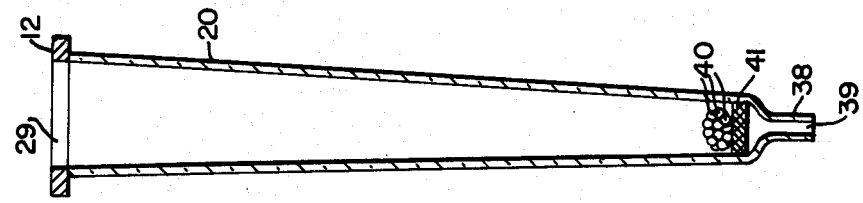
Fig. 2
Fig. 3

SELF-CONTAINED REAGENT PACKAGE DEVICE AND AN ASSAY USING SAME

BACKGROUND OF THE INVENTION

1. Field of the Invention

The present invention relates to a device for performing an assay, and more particularly concerns a self-contained reagent package device useful in the performance of chemical and biological assays, and further relates to the method for the performance of such assays.

2. Description of the Prior Art

Test devices and procedures for assaying chemical and biological liquids are commonly known and used in laboratory practices. Assays are performed to determine trace amounts of many organic materials including drugs, contaminants, pollutants and the like. Similarly, assays are performed on biological liquids such as serum, urine, cerebrospinal fluid, peritoneal exudates, and the like. Different types of assays have been employed depending upon the analyte of interest, and include radioimmunoassays (RIA), enzyme-linked immuno-sorbent assays (ELISA), immunoradiometric assay (IRMA), immunofluorometric assay (IFMA), and other various immunoassays.

Even though assays have been carried out for many years and there are devices which seek to simplify and accurately perform the assays, the need continues for further improvement in assay devices. For example, cross-contamination still remains troublesome, as well as delays for reagent changeover during the assay procedures. Frequent transfer or the pipetting of materials is still involved which could cause inaccuracies of the results. Further, the preparation and pattern of using reagents causes drawbacks in the methodology of the assay procedures, particularly if specific agents are required in non-specialized laboratories.

Various assay devices and procedures have been taught in the prior art. For example, U.S. Pat. No. 3,825,410 describes a disposable combined storage and reaction cell for use in the performance of chemical and biological reactions. This reaction cell is designed to facilitate dispensing the reactants into a container of suitable size and form and the stabilization of the reactants so dispensed. Improvements in storage and transportation under various conditions of temperature and humidity are also described. The patented invention further provides for the addition of sample diluent or other agents and the initiation of the reaction, and finally the separation of the component to be measured from the other components of the reaction.

In U.S. Pat. No. 4,090,850, an apparatus is described for use in radioimmunoassays. Such apparatus includes a receptacle tray with a multiplicity of wells. Each of the wells has at its bottom an orifice sized and shaped to retain the liquids used in the assay under given pressure conditions. The orifice, however, permits the evacuation of liquids therethrough at reduced pressure. This patented invention is said to simplify the manipulative steps that the laboratory technician must use, as well as obviate the need for aspiration of the liquids to be tested.

A test apparatus for the determination of immunoassays of antigens and antibodies is described in U.S. Pat. No. 3,932,141. In this invention, the apparatus includes a receptacle tray with a plurality of wells for receiving samples, and balls coated with an immunological composition. Use of these coated balls is said to effectuate improvements in reproducibility and exactness in radioimmunoassay techniques.

In U.S. Pat. No. 4,160,803, a self-packaged test kit is described. The self-packaged structure is used as a kit for handling and carrying out tests utilizing collection tubes and fraction columns, including a plurality of modular laboratory racks.

An automatic enzyme immunoassay apparatus is described in U.S. Pat. No. 4,383,041. This apparatus includes a rack for holding test tubes; in the test tubes are beads which provide surfaces for the immunochemical reactions.

Notwithstanding the devices and procedures described in the aforementioned prior art, as well as other known and used assay devices, there is room for further improvement in this area. It is to such improvements that the present invention is directed.

SUMMARY OF THE INVENTION

The self-contained reagent package device of the present invention is useful for an assay and includes a support member and a plurality of wells in the support member. All of the wells are capable of retaining liquids therein. At least one of the wells has an aperture at its bottom end for the passage of liquids therethrough. Each well with an aperture includes a carrier to which a reagent is bound and further includes a porous filter positioned between the carrier and the aperture. This filter is capable of retaining the liquids used in the assay under normal atmospheric pressure conditions, but permitting the passage of those liquids, including unbound and soluble substances, at increased pressure within the at least one well. The filter is further capable of retaining the carrier and substances bound thereto. At least one of the wells has a closed bottom and includes a predetermined amount of reagent therein. Another of the wells has a closed bottom and is empty so that the specimen to be assayed may be deposited therein. A removable protective cover is sealed over the open ends of the wells to maintain the incorporated reagents in stable form prior to use.

Another aspect of the present invention is an assay which uses a self-contained reagent package device substantially as described above. The assay steps include depositing the liquid specimen to be assayed in the empty well and removing the protective cover from the open tops of the wells. A measured amount of liquid specimen is transferred to one of the wells with a closed bottom having a reagent therein, thereby forming a mixture. Next, the method includes transferring a measured amount of the mixture to the one well with the aperture and filter so that the mixture reacts with the reagent on the carrier and causes select substances to bind to the carrier. The unbound and soluble substances are removed from the one well through the filter and the aperture, with the filter preventing the passage of the carrier with bound substances. Bound substances are eluted from the carrier and are removed from the well through the filter and the aperture. The method further includes quantifying the bound substances collected from the one well.

In a further aspect of the present invention, a self-contained reagent package and calibration assembly includes a plurality of reagent package devices, substantially as described above, and a reagent standards device. The reagent standards device comprises a support strip from which depends a plurality of receptacles linearly arranged in single file. Each receptacle has an open top end sealed closed by a removable protective cover. In addition, each receptacle has a reagent therein of known character to serve as a calibrator for one of the reagent package devices. Each receptacle is sized to slidably fit into the empty specimen well of a different reagent package device so that calibration of a plurality of reagent package devices may be performed during a single procedure.

In accordance with the principles of the present invention, a self-contained reagent package device and an assay for using same are provided. While many advantages and features result from the present invention, which will become apparent from a reading of the description which follows, there are some notable distinctions that should be mentioned. For example, all reagents for the assay procedure of interest, including the reagent on the carrier, are specific to that assay and are self-contained in the package. This ameliorates problems involved in assay to assay changeover, and means that an assay may be performed with no delay for reagent change-over. Moreover, since beads are the preferred carrier for the reagent in the well with the filter, the beads need not be pipetted or transferred through tubing, thereby preventing any potential inaccuracies of results. Furthermore, the filter incorporated in the present invention may be used several times in the course of assaying a single sample (but should not be used for multiple samples). The configuration of the present invention is versatile thereby allowing a wide selection of wells, filter materials and reagents which may all be selected so as to be assay specific. Various bead sizes, densities and types may be utilized with a given reagent package device of the present invention. Laboratory use of the present device is simplified and straightforward.

BRIEF DESCRIPTION OF THE DRAWINGS

FIG. 2 is a perspective view of the device of FIG. 1 with the protective cover removed;

FIG. 3 is a cross-sectional view of the well with the filter and aperture taken along line 3—3 of FIG. 2.

DETAILED DESCRIPTION

Figure 1:
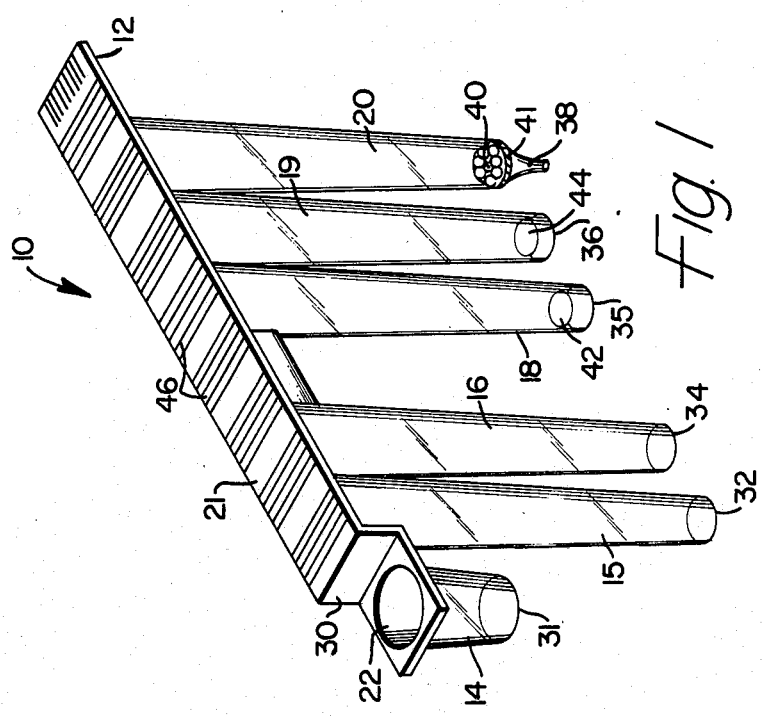
FIG. 1 is a perspective view of the preferred self-contained reagent package device of the present invention.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting now to the drawings, and FIGS. 1 and 2 in particular, there is illustrated the preferred self-contained reagent package device 10. Comprising this device are three major components: a rack 12, a plurality of wells herein designated by the numerals 14,15,16,18,19 and 20, and a removable protective cover 21.

Rack 12, in the embodiment being described, is preferably a substantially planar strip of material having sufficient rigidity to maintain the wells in fixed position for the performance of the various tests. In this embodiment, the wells are linearly arranged in single file in the rack so that the top ends of the wells are joined to the rack while the bottom ends of the wells depend freely downwardly. This free arrangement of the bottom ends of the wells allows the wells to be positioned in a suitable stand during use and also allows clear visual observation of the contents of the wells, particularly if they are made out of transparent material. It can be seen that all of the wells have open top ends for access into the wells, these openings designated by numerals 22,24,25,26,28 and 29, corresponding respectively with each of the wells. Except for well 14 and its open end 22, all of the open top ends of the wells lie substantially in the same plane and, as illustrated, are substantially coextensive with the planar rack. With respect to well 14, it can be seen that the rack, at one end, is formed with a step 30 so as to downwardly displace that end of the rack along with well 14 and its open top end 22.

For purposes of the present invention, it is preferred that all of the wells, except for well 20 at the opposite end of the rack from the stepped well, have closed bottom ends, designated by numerals 31,32,34,35 and 36, corresponding respectively to each of the wells. While closed bottom ends of the wells are preferred, it is understood that one or more of the wells may use the same configuration as well 20 which will now be described.

As seen in the drawings, well 20, positioned at one end of rack 12, has a bottom end 38 which includes an aperture 39 therethrough so that materials may ultimately pass out of well 20 through its bottom end. It can be seen that bottom end 38 of well 20 is tapered so that aperture 39 resembles a channel.

Included in the bottom of well 20 is a reagent carrier, which is preferably in the form of one or more spherical beads 40. These beads are coated in known fashion with a reagent which causes a reaction during the assay procedure. Typically, beads 40 are coated with an immunologic composition such as either an antigen or antibody. When the reaction occurs in well 20 during the assay procedure substances will become bound to the surface of the beads in known fashion. The choice of reagent for coating on the beads depends upon the assay for which the given package device is intended.

Positioned within well 20 between beads 40 and aperture 39 is a porous filter 41. This filter has a pore size or rating which will retain the liquids, used in the assay procedure, within well 20 under normal atmospheric pressure conditions. Retention is achieved by the nature of the pores, and is facilitated by the fact that the filter may be treated to render it hydropholic. On the other hand, with increaed pressure within well 20, the passage of those liquids is permitted through the pores of the filter. Decreased pressure outside of the well will also accomplish the same result. The beads and substances bound thereto are also prevented from passing through filter 41 when liquids are removed from well 20. Unbound or soluble substances are permitted to readily pass through the pores of filter 41 so that their removal from the well produces an effective separation of the components of the reaction whereby the selected component of interest (that bound to the beads) may remain in the well until such time as it is eluted. Filter 41 may be selected to be used by itself if it is of such character as to have sufficient strength to perform its function. On the other hand, it is also within the purview of the present invention to provide a filter support, if necessary, to assure its proper function during the assay procedures.

With respect to the other wells, they may either be empty or contain other liquids or reagents. Well 14 at the stepped end of the rack, for example, is preferably left empty so that the specimen to be assayed may be deposited therein. Depending upon the specific assay to be performed, and merely for exemplary purposes, well 15 may contain an elution buffer or a substrate; well 16 may remain empty for pre-incubation or dilution, if required; well 18 may contain a diluent 42, if required; and well 19 may contain a tracer 44 if necessary for the particular assay. Of course, different materials, reagents, liquids and the like, as well as different numbers of wells, may be selected for the particular assay to be performed.

To provide a self-contained reagent package, removable cover 21 is provided. This cover is sealed to the planar surface of rack 12 so as to effectively close open top ends 24,25,26,28 and 29 of the wells corresponding respectively thereto. It is preferred that removable cover 21 leave top end 22 of the well 14 uncovered since that well is preferably empty and is in ready condition to accept the specimen to be assayed. Cover 21 may be affixed to rack 12 by any convenient mechanism for assuring a tight seal while allowing the cover to be removed when the device is ready for use. A finger notch 45 is included in one end of rack 12 so as to facilitate the gripping of the end of cover 21 for removal purposes.

It can be seen in the drawings that protective cover 21 includes labeling information 46 on its upper surface. This labeling information may identify the various reagents contained within the wells, the type of assay to be performed, dates of manufacture and use, and other information that may be useful for information control purposes. In the embodiment being described, it is preferred that the labeling information be in the form of a bar code adapted to be read electronically to determine the information imprinted thereon. These bar codes are well-known and the information with respect to different bar configurations may be pre-programmed into a microprocessor so that once a recognizable code has been electronically read, that information may be retrieved, displayed, stored or otherwise acknowledged.

As a self-contained reagent package device, the present invention maintains the incorporated reagents in stable form prior to use. A typical assay procedure in which device 10 is used will now be described. This typical assay procedure is merely exemplary as it may relate to the one configuration of the reagent package device illustrated in the drawings. No limitations with respect to the scope of the present invention should be attributed to the following description.

If, for example, blood serum is to be assayed for a determination of trace amounts of proteins, hormones, drugs or the like, the prepared serum is deposited in well 14. Either before the specimen is placed in well 14 or immediately thereafter, protective cover 21 is removed from rack 12 so as to expose the open top ends of the remaining wells of the pre-packaged device. A measured amount of the serum is withdrawn from well 14 and transferred to well 18, for example, which contains a diluent. Once diluted in well 18, a measured amount of the diluted specimen is withdrawn and transferred to well 19 which, for example, may include a tracer material, which causes a reaction with one or more components of the diluted serum. Radioactive, fluorescent and the like materials are typically used as tracers.

After sufficient time has passed to allow the tracer to react with the components of diluted serum, a measured amount of the reacted mixture in well 19 may be withdrawn and deposited in well 20. Previously packaged within well 20 is one or more beads to which a particular reagent is bound. Typically, an antigen or an antibody is bound to the surface of the beads. The mixture with tracer then reacts with the reagent on the beads and the antibody/antigen reaction causes select substances to bind to the surface of the beads. A wash usually follows in which an appropriate liquid under positive pressure is introduced into well 20 thereby driving unbound substances as well as soluble substances in the liquid medium out of well 20 through its aperture 39. The beads which are larger than the pores of filter 41 are prevented from passing out of the aperture. Of course, those substances bound to the surfaces of the beads also remain within well 20 after the wash.

In order to obtain the substances bound to the beads, an elution step is normally performed. An elution buffer contained in well 15 is withdrawn and transferred to well 20. As a result, the substances adsorbed on the beads are removed by virtue of the elution solvent. Then, under positive pressure provided to the interior of well 20, or negative pressure applied to the exterior of well 20, these originally bound substances now pass through filter 41 and aperture 39 and may be collected for quantification, further analysis or testing. It is clear that different mixtures, reactions, liquid transfer steps and other assay procedures may be employed with the present invention. Further, as long as a single sample is being assayed, well 20 and its filter 41 may be used several times by the laboratory technician.

Figure 4:
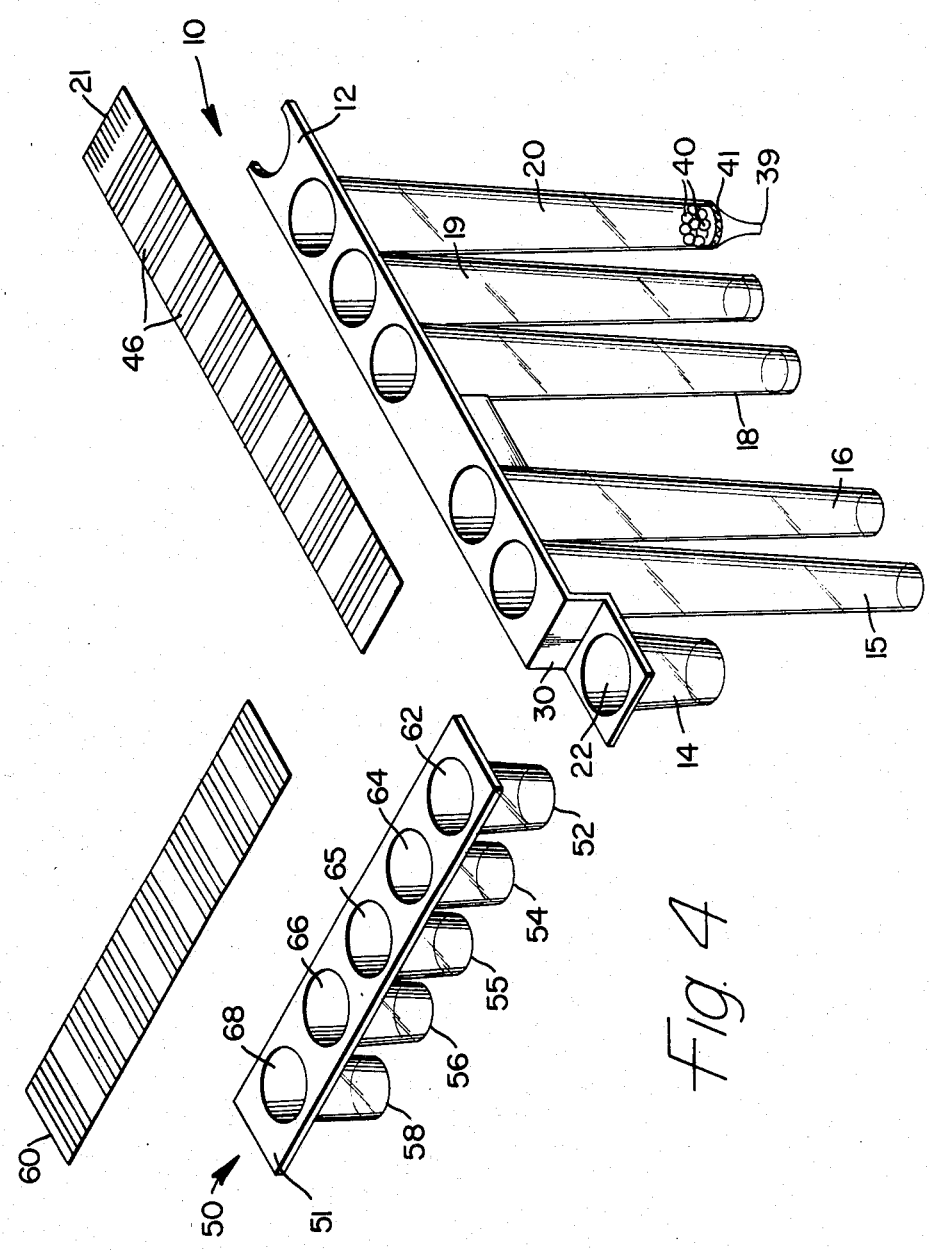
FIG. 4 is a perspective view of the preferred self-contained reagent package device illustrated together as an exploded assembly with a reagent standards device for calibration purposes.

The self-contained reagent package device of the present invention further lends itself to being readily calibrated using known reagent standards. For instance, as illustrated in FIG. 4, a self-contained reagent standards device 50 may be provided for use with a plurality of the reagent package devices of the present invention. Reagent standards device 50 also includes three major components: a support strip 51, a plurality of receptacles such as those designated by numerals 52,54,55,56 and 58, and a removable protective cover 60. Cover 60 is in substantially all respects similar to removable cover 21 for the reagent package device. Cover 60 further includes labeling information on its top surface with such labeling information preferably in the form of a bar code so as to be read electronically. The receptacles are preferably linearly arranged in single file and depend downwardly from support strip 51. Each receptacle has an open top end designated by numerals 62,64,65,66 and 68 corresponding to their respective receptacles. Included in each receptacle, in pre-packaged form, is a reagent of known character representing a standard to which the subsequently assayed materials will be compared. Protective cover 60, sealed over the open top ends of the receptacles with reagents therein, maintains these reagents in stable form prior to use of the device.

Each receptacle of device 50 is sized to slidable fit into the empty specimen well of the reagent package device. As seen in FIG. 4, standards device 50 would be aligned at substantially right angles to reagent package device 10 so that receptacle 52 slidably enters empty well 14 through its open top end 22. Another reagent package device (not shown) would be positioned next to the first package device so that receptacle 54 would slidably fit into its empty specimen well. In this fashion, an array of reagent package devices may be calibrated corresponding to the number of receptacles in the reagent standards device. This arrangement provides a convenient mechanism for calibrating a number of different substances for the assay procedures to be performed on the specimen of interest.

While many different materials may be used to construct the rack and wells of the reagent package device as well as the strip member and receptacles of the reagent standards device. plastic is the material of choice. Preferably, a rigid, transparent plastic, such as clear polypropylene, is selected for the present invention. Use of plastic material also allows the rack and wells to be formed in a molding operation. As a result, the rack and wells are preferably integrally formed as a unitary structure. This not only facilitates the manufacturing operation, but allows the device to be inexpensively made so as to render it disposable after use.

Carrier 40 inside well 20 may also be selected from different materials depending upon the type of assay to be performed. Plastic beads are preferred since reagents, such as immunologic compositions, may be readily attached to the surface of the beads. Polystyrene beads are known and available for these purposes. Different bead sizes, densities and types may be selected, again depending upon the type of assay to be performed.

Filter 41 is selected to have a pore size or rating to prevent the passage of liquids under normal atmospheric pressure conditions, as well as the carrier material, while permitting the passage of soluble substances and unbound components of the specimen being assayed. Materials out of which filter 41 may be formed include tetrafluoroethylene, polypropylene and ultra high molecular weight polyethylene. For the various assays which may be performed, the pore size of the filter may range from 0.5 to 10 microns. Various reagents, liquids and other materials may be incorporated in the present device in prepackaged form, and the number of wells may be varied according to the specific assay desired.

Thus, the present invention provides a self-contained reagent package device wherein all of the reagents necessary for the assay are pre-prepared for ease of use by the laboratory technician. The carrier beads preferably used in the present invention need not be pipetted or moved through tubing, thereby preventing potential inaccuracies of measurement. Inasmuch as the filter of the present invention is contacted by only a single sample, cross-contamination, reagent carryover and plugging are eliminated, thereby significantly increasing the simplification of the assay procedure. Furthermore, the filter may be used a number of times when assaying a single sample, but, of course, should not be used for multiple samples.

What is claimed is:

1. A self-contained reagent package device useful in the performance of chemical and biological assays comprising:
    a rack;
    a plurality of wells in said rack, all of said wells having open top ends for access thereto, and all but one of said wells having closed bottom ends, said one well having an aperture at its bottom end for the passage of liquids therethrough, said one well including beads to which a reagent is bound and further including a porous filter positioned between said beads and said aperture which is constructed so as to retain liquids used in the assay under normal atmospheric pressure conditions but permitting the passage of said liquids, including unbound and soluble substances, therethrough at increased pressure within said one well, said filter further being constructed so as to retain the beads and substances bound thereto;
    at least one of said wells with a closed bottom having a predetermined amount of reagent therein;
    another of said wells with a closed bottom being empty so that the specimen to be assayed may be deposited therein; and
    a removable protective cover sealed over the open ends of said wells to maintain the incorporated reagents in stable form prior to use thereby providing a self-contained reagent package device.

2. The device of claim 1 wherein the open top ends of said wells lie substantially in the same plane.

3. The device of claim 2 wherein said rack is a substantially planar strip member having the open top ends of said wells coextensive therewith.

4. The device of claim 3 wherein said wells are linearly arranged in single file in said rack.

5. The device of claim 4 wherein said one well is positioned at one end of said rack and said empty well for the specimen is positioned at the other end of the rack.

6. The device of claim 5 wherein the open top end of said empty specimen well is downwardly displaced with respect to the top ends of the remaining wells.

7. The device of claim 1 wherein the removable cover is positioned such that the open top end of said empty specimen well remains uncovered and open for access prior to the removal of said cover for using of the device.

8. The device of claim 1 wherein said rack and said wells are made of rigid plastic.

9. The device of claim 8 wherein said rack and said wells are integrally formed as a unitary structure.

10. The device of claim 1 wherein said protective cover includes labeling information thereon which is related to the nature of an assay to be performed.

11. The device of claim 10 wherein said information is in the form of a bar code constructed and arranged so as to be read electronically to determine said information.

12. The device of claim 1 wherein said beads are made of plastic and said reagent bound thereto is an immunologic composition.

13. The device of claim 1 wherein said filter is made of tetrafluoroethylene and has a pore rating between 0.5 and 10 microns.

14. A self-contained reagent package device for an assay comprising:
    a support member;
    a plurality of wells in said support member, all of said wells being constructed so as to retain liquids therein under normal atmospheric pressure conditions, at least one of said wells having an aperature at its bottom end for the passage of liquids therethrough;
    a carrier to which a reagent is bound in said at least one well with an aperture;
    a porous filter positioned between said carrier and said aperture which is constructed so as to retain liquids used in the assay under normal atmospheric pressure conditions but permitting the passage of said liquids, including unbound and soluble substances, therethrough at increased pressure within said one well, said filter further being constructed so as to retain the carrier and substances bound thereto;

at least one of said wells including a predetermined amount of reagent therein;

another of said wells being empty so that the specimen to be assayed may be deposited therein; and a removable protective cover sealed over the open ends of said wells to maintain the incorporated reagents in stable form prior to use.

15. A self-contained reagent package device useful in the performance of chemical and biological assays comprising:

a substantially planar strip member serving as a rack;

a plurality of wells integrally formed and linearly arranged in single file in said rack, all of said wells having top ends for access thereto, all the open top ends of said wells, except for one such open top at a first end of said rack, lying in substantially the same plane coextensive with the rack, the open top of the well at said first end being displaced downwardly with respect to the top ends of the remaining wells, all but one of said wells having closed bottom ends, said one well positioned at the opposite end of said rack and having an aperture at its bottom end for the passage of liquids therethrough, the well with said aperture including beads to which a reagent is bound and further including a porous filter positioned between said beads and said aperture which is constructed so as to retain liquids used in the assay under normal atmospheric pressure conditions but permitting the passage of said liquids, including unbound and soluble substances, therethrough at increased pressure within said one well, said filter further being constructed so as to retain the beads and substances bound thereto;

at least one of said wells with a closed bottom, other than said wells at the respective ends of the rack, having a predetermined amount of reagent therein;

said well at the first end of the rack being empty so that the specimen to be assayed may be deposited therein; and a removable protective cover sealed over the open ends of said wells except said empty specimen well to maintain the incorporated reagents in stable form prior to use, said cover including labeling information thereon in the form of a bar code constructed and arranged so as to be read electronically to determine said information.

16. A self-contained reagent package and calibration assembly including a plurality of reagent package devices and a reagent standards device, each reagent package device comprising:

a support member a plurality of wells in said support member, all of said wells being constructed so as to retain liquids therein under normal atmospheric pressure conditions, at least one of said wells having an aperture at its bottom end for the passage of liquids therethrough;

a carrier to which a reagent is bound in said at least one well with an aperture;

a porous filter positioned between said carrier and said aperture which is constructed so as to retain liquids used in the assay under normal atmospheric pressure conditions but permitting the passage of said liquids, including unbound and soluble substances, therethrough at increased pressure within said one well, said filter further being constructed so as to retain the carrier and substances bound thereto;

at least one of said wells including a predetermined amount of reagent therein;

another of said wells being empty so that the specimen to be assayed may be deposited therein; and a removable protective cover sealed over all the open ends of the wells except said empty specimen well to maintain the incorporated reagents in stable form prior to use;

said reagent standards device comprising:

a support strip from which depends a plurality of receptacles linearly arranged in single file, each receptacle having an open top end sealed closed by a removable protective cover and each receptacle having a reagent therein of known character to serve as a calibrator for one of said reagent package devices, each receptacle sized to slidably fit into the empty specimen well of a different reagent package device so that calibration of a plurality of reagent package devices may be performed during a single procedure.

17. An assay procedure using a self-contained reagent package device including:

a support member;

a plurality of wells in said support member, all of said wells being constructed so as to retain liquids therein under normal atmospheric pressure conditions, at least one of said wells having an aperture at its bottom end for the passage of liquids therethrough;

a carrier to which a reagent is bound in said at least one well with an aperture;

a porous filter positioned between the carrier and the aperture which is constructed so as to retain liquids used in the assay under normal atmospheric pressure conditions but permitting the passage of said liquids, including unbound and soluble substances, therethrough at increased pressure within said one well, said filter further being constructed so as to retain the carrier and substances bound thereto;

at least one of said wells including a predetermined amounts of reagent therein;

another of said wells being empty so that the specimen to be assayed may be deposited therein; and a removable protective cover sealed over the open ends of said wells to maintain the incorporated reagents in stable form prior to use, said assay comprising the steps of:

depositing the liquid specimen to be assayed in said empty well;

removing said protective cover from the open tops of said wells;

transferring a measured amount of liquid specimen to one of said wells having a reagent therein to thereby form a mixture;

transferring a measured amount of said mixture to said one well with the aperture and filter so that said mixture reacts with the reagent on said carrier and causes select substances to bind to said carrier;

removing the unbound and soluble substances from said one well through said filter and said aperture, said filter preventing the passage of the carrier with bound sustances;

eluting the bound substances from the carrier and removing same from said wells through said filter and said aperture; and quantifying the bound substrates collected from said one well.

18. The assay procedure of claim 17 wherein said substances are removed from said one well through its aperture by applying positive pressure to the interior of said one well.

19. The assay procedure of claim 17 wherein said substances are removed from said one well through its aperture by applying negative pressure to the exterior of said one well.

20. The assay procedure of claim 17 which further includes a plurality of intermediate transfer steps of said liquid specimen into at least one of said plurality of wells prior to its introduction into said one well with the aperture and filter.

21. The assay procedure of claim 17 wherein both of the transferring steps, the removing step and eluting step are repeated a plurality of times in assaying the liquid specimen deposited in the empty well.

* * * * *